Figure 1:
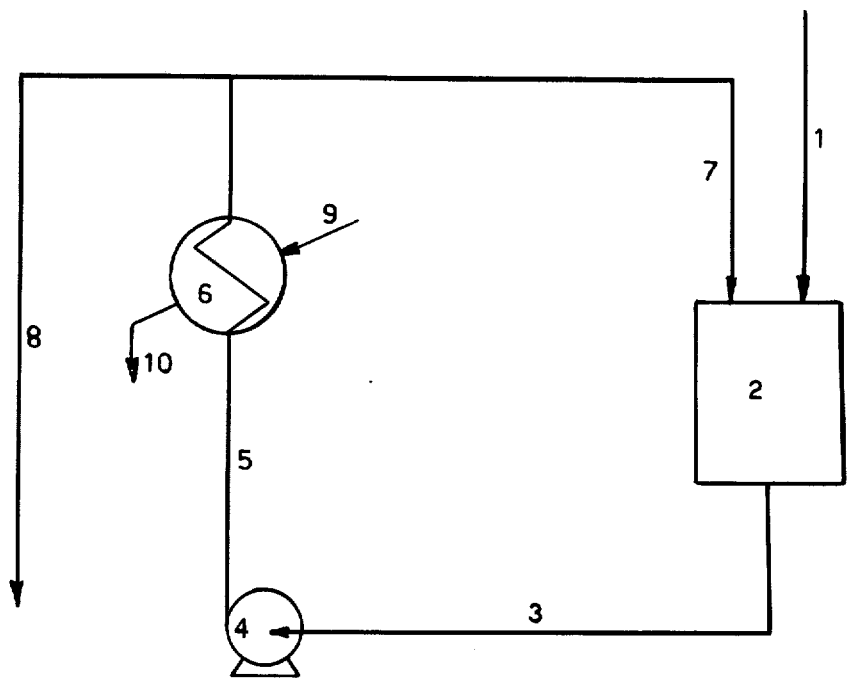

United States Patent [19]
Zardi et al.

[11] 3,936,499
[45] Feb. 3, 1976

[54] PROCESS FOR THE PRODUCTION OF PRILLED UREA HAVING A LOW BIURET CONTENT

[75] Inventors: Umberto Zardi, San Donato Milanese; Vincenzo Lagana; Carlo Mantegazza, both of Milan, all of Italy

[73] Assignee: Snam progetti S.p.A., San Donato Milanese, Italy

[22] Filed: May 21, 1970

[21] Appl. No.: 39,292

[30] Foreign Application Priority Data
May 29, 1969 Italy.................................. 17499/69

[52] U.S. Cl. .......................... 260/555 C; 260/555 B
[51] Int. Cl.² ........................................ C07C 126/00
[58] Field of Search ....... 260/555 C, 555 B; 264/13, 264/14; 159/47 UA

[56] References Cited
UNITED STATES PATENTS
| | | | |
|---|---|---|---|
| 3,025,571 | 3/1962 | Beecher et al. | 260/555 B |
| 3,398,191 | 8/1968 | Thompson et al. | 260/555 C |

*Primary Examiner*—James O. Thomas, Jr.
*Assistant Examiner*—A. Siegel
*Attorney, Agent, or Firm*—Ralph M. Watson, Esq.

[57] ABSTRACT

A process is described wherein prilled urea of low biuret content is prepared by crystallizing urea of low biuret content by melting from only 30 to 70 percent of the urea crystals through the application of heat thereto, and forming a heterogeneous mixture of the unmelted crystals in the melted urea. That mixture is then fed to conventional pelleting apparatus.

2 Claims, 1 Drawing Figure

U.S. Patent  February 3, 1976  3,936,499

PROCESS FOR THE PRODUCTION OF PRILLED UREA HAVING A LOW BIURET CONTENT

The present invention relates to a process for the production of prilled urea from melted urea with a very low increase in biuret content.

It is well known that in several uses of urea a high purity degree is required, particularly a very low biuret content.

Several methods for obtaining high purity urea are known; the most known one provides the production of urea crystals.

In the apparatus for crystallizing urea solution, also with high biuret concentration, pure crystals of urea develop and the content of impurities is limited on the surfaces where the mother liquor covers the crystals.

It is sufficient therefore to wash said crystals to obtain a high purity product.

Crystals are however generally subject to packing and therefore urea is usually in demand by the market in prills.

Said kind of product, i.e., prills, is much more suitable from the point of view of the handling and presents no problems of packing when stored in bags or in bulk.

For these two reasons urea is generally preferred in prills and not in crystals.

To obtain a product in prills with a low biuret content use is made of a production cycle which allows to obtain urea as high purity crystals; said crystals are then melted and the melted urea is prilled with techniques known in the art.

The melted urea tends however to give biuret according to following quick reaction:

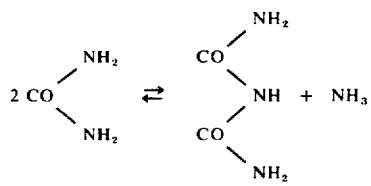

Therefore the melting of urea crystals is the most critical stage in the above techniques as said stage must be carried out with a minimum increase in biuret content so as to have a final product presenting a high purity.

The market of low biuret content urea requires usually a product with a maximum 0.3 percent biuret content.

Object of the present invention is a method for melting urea crystals so as to minimize the biuret content increase occurring during the melting and at the same time to reduce the heat consumption.

The above advantages are achieved by using a method in which only a partial melting of the crystals is provided so as to obtain crystals in suspension in melted urea suitable to be prilled by known method.

The tests, we carried out, had shown that it is possible to avoid to feed the pelleting apparatus with completely melted urea.

In fact it is possible to operate with melted urea having crystals in suspension, in this way not only it is possible to utilize known pelleting apparatus but the product obtained presents excellent mechanical properties.

The process according to the present invention comprises the following fundamental zones:

1. A melting zone where crystals are melted by heat supplying.
2. A zone where melted urea is mixed with crystals fed to the apparatus.
3. A system to control the ratio between melted urea and crystals in suspension.

The advantages obtained with the process according to the present invention, i.e., the partial fusion of the urea crystals, are the following ones:

1. A lower increase of the biuret content during the melting since the portion of not melted crystals keeps its biuret content equal to the initial value.

The biuret content in the heterogeneous mixture melted urea — urea crystals is much lower than the content when the crystals are completely and wholly melted.

2. A high reduction of heat consumption since it is necessary to supply only the heat necessary to melt only part of the crystals introduced into the apparatus.

For illustrative purpose only reference is made to the following example specifying, with reference to the enclosed drawing, a realization of the present invention.

It will be clear that other realizations of the present invention are possible and that the following example is not restrictive.

EXAMPLE

Through line 1 urea crystals with a 0.05% biuret content are fed to the mixer 2, said crystals being at a temperature of 90°C.

Through line 7 melted urea with crystals in suspension is also fed to mixer 2, this heterogeneous mixture is circulated through conduit 3 by means of pump 4 sent, through 5, to the heat exchanger 6 supplied with the heat necessary to melt the requested amount of crystals; said amount is controlled by the heating fluid flow rate and by the outlet temperature of this fluid from the exchanger. The heating fluid enters through 9 and leaves through 10.

The melted urea, with 30 percent of crystals in suspension, is in part sent, through 8, to the following treatment of pelleting and the remainder is recycled through line 7 to mixer 2.

While the content of biuret in the urea melted with the method according to the present invention, i.e., melted urea with crystals in suspension, is in a prilling at 138°C of 0.12 percent, the biuret content by employing known methods, i.e., the complete melting of urea crystals, is of 0.25 percent.

The consumption of the steam, entering through 9 the echanger 6, is of 140 kg/ton of urea.

The crystals content in the urea-crystals suspension can be increased up to 70 percent with a further reduction of steam consumption. It depends on the apparatuses employed in the pelleting and on the allowed biuret content.

In known methods said steam consumption is of 200 kg/ton of urea.

What we claim is:

1. A process for the production of prilled urea having a low biuret content comprising the steps of crystallizing urea of low biuret content, melting the resulting crystals and pelleting the melted urea, wherein the improvement comprises supplying to the urea crystals to be pelleted sufficient heat to melt from only 30% to 70% of said crystals, forming therefrom a heterogeneous mixture of melted urea with crystals in suspension, and feeding said mixture to pelleting apparatus.

2. A process for the production of prilled urea having a low biuret content according to claim 1 wherein the residual content of crystals in the mixture of melted urea does not exceed 70 percent by weight.

\* \* \* \* \*